(12) United States Patent
Yamamoto et al.

(10) Patent No.: US 8,540,368 B2
(45) Date of Patent: Sep. 24, 2013

(54) OPHTHALMIC PHOTOGRAPHING APPARATUS

(75) Inventors: Mitsuo Yamamoto, Gamagori (JP); Seiji Taki, Okazaki (JP); Norimasa Satake, Nukata-gun (JP)

(73) Assignee: Nidek Co., Ltd., Gamagori (JP)

( * ) Notice: Subject to any disclaimer, the term of this patent is extended or adjusted under 35 U.S.C. 154(b) by 165 days.

(21) Appl. No.: 12/801,282

(22) Filed: Jun. 1, 2010

(65) Prior Publication Data

US 2010/0302508 A1  Dec. 2, 2010

(30) Foreign Application Priority Data

Jun. 2, 2009  (JP) .................... 2009-133534

(51) Int. Cl.
*A61B 3/10* (2006.01)
*A61B 3/14* (2006.01)

(52) U.S. Cl.
USPC ........................................ 351/206; 351/205

(58) Field of Classification Search
USPC ............... 351/205, 206, 221; 356/450, 477, 356/479; 382/131; 600/407, 425
See application file for complete search history.

(56) References Cited

U.S. PATENT DOCUMENTS

| 7,510,282 B2 | 3/2009 | Ueno et al. |
| 2007/0188707 A1 | 8/2007 | Nanjo |
| 2007/0268456 A1* | 11/2007 | Ohbayshi et al. ............. 351/246 |
| 2008/0100612 A1 | 5/2008 | Dastmalchi et al. |
| 2008/0204655 A1* | 8/2008 | Kikawa et al. ................ 351/206 |

FOREIGN PATENT DOCUMENTS

| EP | 1 836 953 A1 | 9/2007 |
| EP | 1 952 755 A1 | 8/2008 |
| EP | 1 961 374 A1 | 8/2008 |
| EP | 1 972 265 A2 | 9/2008 |
| JP | A-2006-212153 | 8/2006 |
| JP | A-2008-029467 | 2/2008 |

* cited by examiner

*Primary Examiner* — Mahidere Sahle
(74) *Attorney, Agent, or Firm* — Oliff & Berridge, PLC

(57) ABSTRACT

An ophthalmic photographing apparatus including an interference optical system for dividing light from a first light source into measurement light and reference light, directing measurement light to a fundus and reference light to a reference optical system, and photo-receiving by a first photodetector interference light, a first optical scanner disposed in a measurement light optical path and scanning measurement light in two dimensional directions, a driving unit moving an optical member in an optical path of measurement light or reference light to change an optical path length, a control unit controlling the driving unit to adjust an optical path length difference, controlling the optical scanner to scan measurement light at a given photographing view angle, and obtaining a tomographic image based on a photodetector signal, and a calculation unit converting a photographing range into an actual distance based on optical member positional information and view angle information.

6 Claims, 2 Drawing Sheets

OPHTHALMIC PHOTOGRAPHING APPARATUS

BACKGROUND OF THE INVENTION

1. Field of the Invention

The present invention relates to an ophthalmic photographing apparatus arranged to photograph a fundus of an examinee's eye.

2. Description of Related Art

Conventionally, as an ophthalmic photographing apparatus arranged to obtain a tomographic image of an examinee's eye in a non-invasive method, there is known an optical coherence tomography (OCT) apparatus using low coherent light. There is proposed an ophthalmic photographing apparatus arranged to obtain a tomographic image and a front image of a fundus that combines an optical system of the OCT apparatus described above with a scanning laser opthalmoscope (SLO) optical system or an observation optical system capable of obtaining the fundus front image such as a fundus camera optical system (see Japanese Patent Application Laid-open Publication No. 2008-29467).

It is considered that if an actual distance of an affected area or other areas of the fundus can be favorably measured by using the fundus front image and the fundus tomographic image that are obtained by the ophthalmic photographing apparatus described above, it becomes possible to perform quantitative evaluation or other operations of a fundus shape (e.g., a shape of a papillary portion), which is useful in diagnosis of the fundus.

SUMMARY OF THE INVENTION

The present invention provides an ophthalmic photographing apparatus arranged to perform favorable fundus measuring.

To achieve the objects and in accordance with the purpose of the present invention, an ophthalmic photographing apparatus has an interference optical system arranged to divide light emitted from a first light source into measurement light and reference light, direct the measurement light to a fundus of an examinee's eye, direct the reference light to a reference optical system, and photo-receive by a first photodetector interference light that is obtained by combining the measurement light reflected from the fundus and the reference light, a second optical scanner disposed in an optical path of the measurement light and arranged to scan the measurement light in two dimensional directions on the fundus, a driving unit arranged to move an optical member disposed in one of the optical path of the measurement light and an optical path of the reference light in order to change an optical path length of the one of the optical paths, a photographing control unit arranged to control an operation of the driving unit to adjust an optical path length difference between the optical path of the measurement light and the optical path of the reference light, control an operation of the first optical scanner to scan the measurement light at a given photographing view angle on the fundus, and obtain a tomographic image of the fundus based on a photo-receiving signal outputted from the first photodetector, and a calculation unit arranged to convert a photographing range of the fundus tomographic image into an actual distance based on positional information on the optical member and information on the photographing view angle of the fundus tomographic image.

Additional objects and advantages of the invention are set forth in the description which follows, are obvious from the description, or may be learned by practicing the invention. The objects and advantages of the invention may be realized and attained by the ophthalmic photographing apparatus in the claims.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

Figure 1:
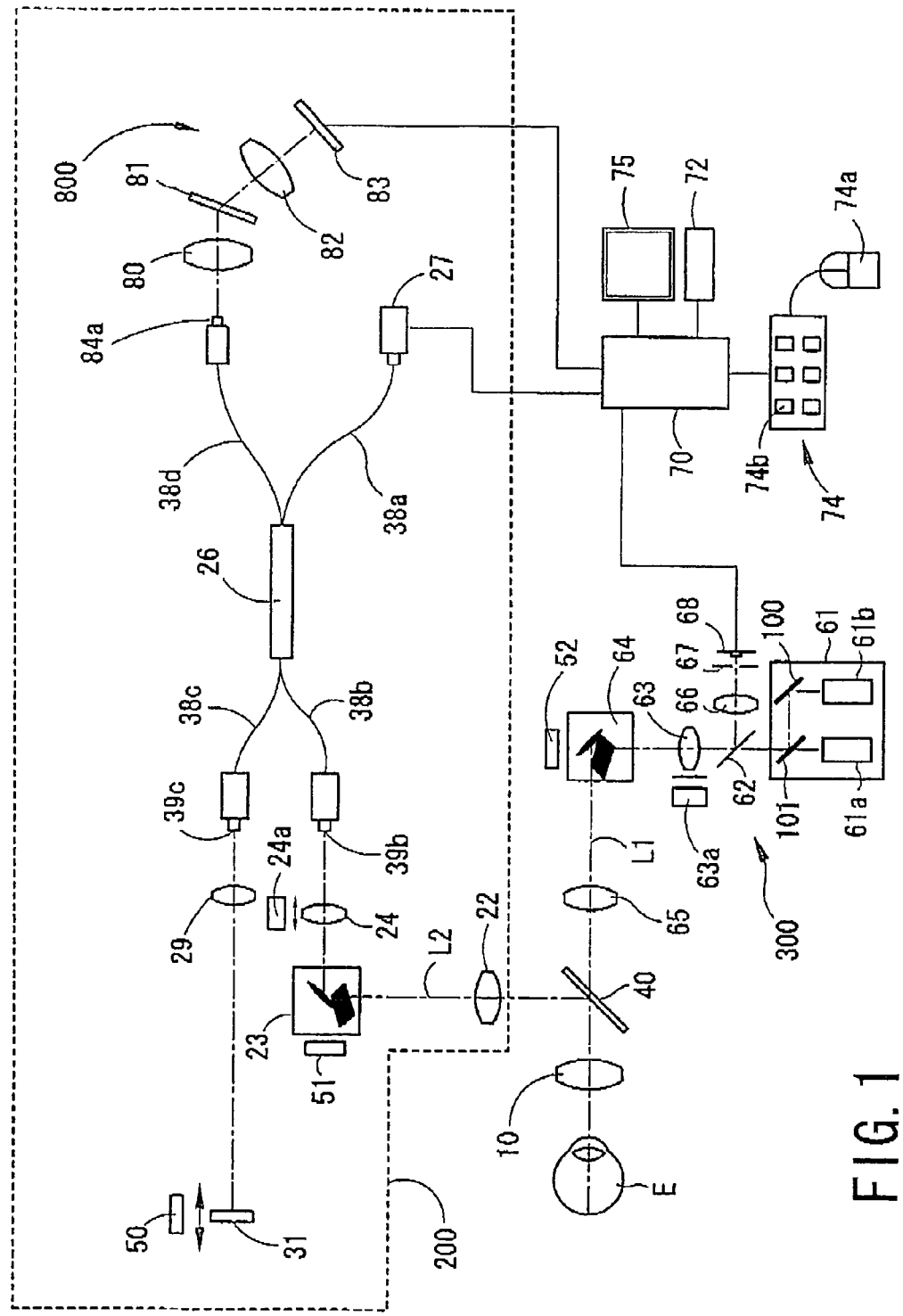
FIG. 1 is a view showing an optical system and a control system of an ophthalmic photographing apparatus according to a preferred embodiment of the present invention.

A detailed description of one preferred embodiment of an ophthalmic photographing apparatus embodied by the present invention is provided below with reference to the accompanying drawings. FIG. 1 is a view showing an optical system and a control system of the ophthalmic photographing apparatus according to the present preferred embodiment of the present invention. In the present preferred embodiment of the present invention, a depth direction of an examinee's eye E is referred to as a Z-direction (a direction of an optical axis L1), a horizontal direction is referred to as an X-direction, and a vertical direction is referred to as a Y-direction.

Referring to FIG. 1, the optical system is roughly divided into an interference optical system 200 arranged to obtain a tomographic image of a fundus of the eye E by an interferometric technique in a non-invasive method (hereinafter, referred to as the OCT optical system 200), and a scanning laser opthalmoscope optical system 300 arranged to obtain an SLO fundus image for observation by illuminating the fundus with infrared light (hereinafter, referred to as the SLO optical system 300). A Fourier-domain OCT optical system is used as the OCT optical system 200.

A dichroic mirror 40 defines a light-dividing member, and has a property of reflecting measurement light which is emitted from a measurement light source 27 of the OCT optical system 200 (e.g., light with wavelengths in the vicinity of 840 nm), and a property of transmitting laser light which is emitted from a light emitting unit 61 of the SLO optical system 300 (light with a wavelength different from the wavelength of the light from the OCT light source 27, e.g., light with wavelengths in the vicinity of 780 nm). The dichroic mirror 40 makes an optical axis L2 of the OCT optical system 200 coaxial with the optical axis L1 of the SLO optical system 300.

First, a description of the OCT optical system 200 which is disposed at a reflection side of the dichroic mirror 40 is provided. The OCT light source 27 is arranged to emit low coherent light to be used as measurement light and reference light of the OCT optical system 200. An SLD light source is preferably used as the OCT light source 27. Specifically, a light source having a center wavelength of 840 nm and a bandwidth of 50 nm is used, for example. A fiber coupler 26 functions as both of a light dividing member and a light combining member. The light from the OCT light source 27 passes through an optical fiber 38a that functions as a light guide, and is divided into the reference light and the measurement light by the fiber coupler 26. The measurement light passes through an optical fiber 38b and heads for the eye E. The reference light passes through an optical fiber 38c and heads for a reference mirror 31.

On an optical path where the measurement light travels to the eye E, an end portion 39b of the optical fiber 38b from which the measurement light exits, a focusing lens 24 which is movable in an optical axis direction in accordance with refractive error of the eye E, a scanning unit 23 which is defined by a combination of two galvano mirrors capable of scanning the measurement light in the X- and Y-directions on the fundus by driving of a scanning driving mechanism 51, and a relay lens 22 are disposed. The dichroic mirror 40 and the objective lens 10 define a light directing optical system arranged to direct the OCT measurement light from the OCT optical system 200 to the fundus. In the scanning unit 23 according to the present preferred embodiment of the present invention, scanning directions of the scanning of the measurement light on the fundus can be arbitrarily set by arbitrarily adjusting reflection angles of the measurement light by using the two galvano mirrors. Thus, a tomographic image of a given portion of the fundus can be obtained. The end portion 39b of the optical fiber 38b is disposed so as to be conjugate with the fundus, and the two galvano mirrors of the scanning unit 23 are disposed at positions substantially conjugate with a pupil of the eye E.

The measurement light reflected from the fundus passes through the objective lens 10, is reflected by the dichroic mirror 40, and heads for the OCT optical system 200, where the measurement light enters the end portion 39b of the optical fiber 38b via the relay lens 22, the two galvano mirrors of the scanning unit 23, and the focusing lens 24. The measurement light which enters the end portion 39b reaches an end portion 84a of an optical fiber 38d via the optical fiber 38b, the fiber coupler 26, and the optical fiber 38d.

On an optical path where the reference light travels to the reference mirror 31, an end portion 39c of the optical fiber 38c from which the reference light exits, a collimator lens 29, and the reference mirror 31 are disposed. The reference mirror 31 is movable in an optical axis direction by a reference-mirror driving unit 50 to change the optical path length of the reference light.

The reference light which is thus formed from the light emitted from the OCT light source 27, and the reflection light from the fundus which is formed from the measurement light with which the fundus is illuminated are combined by the fiber coupler 26 to be made into interference light. Then, after passing through the optical fiber 38d, the interference light exits from the end portion 84a. A spectral optical system (a spectrometer unit) 800 arranged to disperse the interference light into frequency components in order to obtain an interference signal for each of the frequencies includes a collimator lens 80, a grating mirror (a diffraction grating) 81, a condenser lens 82, and a photodetector 83. A one-dimensional detector (a line sensor) which has sensitivity to an infrared range is used as the photodetector 83.

To be specific, the interference light exiting from the end portion 84a is made into parallel light by the collimator lens 80, and then is dispersed into the frequency components by the grating mirror 81. The interference light dispersed into the frequency components is collected on a photo-receiving surface (array) of the photodetector 83 via the condenser lens 82. Thus, spectral information on interference fringes is recorded at the photodetector 83. Then, the spectral information is inputted into a control unit 70, and is analyzed by performing the Fourier transform thereon, whereby information in the depth direction of the eye E (an A-scan signal) can be obtained. The control unit 70 can obtain a tomographic image by controlling the scanning unit 23 to scan the measurement light in a predetermined transverse direction on the fundus. For example, the scanning of the measurement light in the X- or Y-direction allows the control unit 70 to obtain a tomographic image on an X-Z or Y-Z plane of the fundus (in the present preferred embodiment of the present invention, a mode of thus obtaining the tomographic image by one-dimensionally scanning the measurement light on the fundus is referred to as B-scan). The obtained tomographic image is stored in a memory 72 connected to the control unit 70. It is also possible to obtain a three-dimensional image of the fundus by two-dimensionally scanning the measurement light in the X- and Y-directions on the fundus. The obtainment of an OCT image in the present preferred embodiment of the present invention is performed with the use of the two galvano mirrors of the scanning unit 23.

Next, a description of the SLO optical system (a confocal optical system) 300 which is disposed at a transmission side of the dichroic mirror 40 is provided. The SLO optical system 300 is roughly divided into an illumination optical system arranged to illuminate the fundus with light, and a photo-receiving optical system arranged to photo-receive the illumination light reflected from the fundus with the use of a photodetector. The SLO optical system 300 obtains a front image of the fundus based on a photo-receiving signal outputted from the photodetector. The second photographing optical system arranged to obtain the front image of the fundus may have an SLO-based configuration to be described below or a fundus camera-based configuration.

The emitting unit 61 has a first light source (an SLO light source) 61a arranged to emit light in an infrared wavelength range (e.g., light with a wavelength of 780 nm), a second light source (a fixation light source) 61b arranged to emit light in a visible wavelength range (e.g., light with a wavelength of 630 nm), a mirror 100, and a dichroic mirror 101. As the first light source 61a and the second light source 61b, light sources arranged to emit light with high intensity and high directivity (e.g., laser diode light sources and SLD light sources) are used. The infrared light from the first light source 61a passes through the dichroic mirror 101, exits from the emitting unit 61, and heads for a beam splitter 62. The visible light from the second light source 61b is deflected by the mirror 100, and is reflected by the dichroic mirror 101 to be made coaxial with the infrared light from the first light source 61a. The first light source 61a is used for obtaining a front fundus image for observation, and the second light source 61b is used for guiding a line of sight of the eye E.

On an optical path where the laser light (measurement light or fixation light) from the emitting unit 61 travels to the eye E, a focusing lens 63 which is movable in an optical axis direction in accordance with the refractive error of the eye E, a scanning unit 64 which is defined by a combination of a galvano mirror and a polygon mirror capable of rapidly scanning the measurement light in the X- and Y-directions on the fundus by driving of a scanning driving mechanism 52, a relay lens 65, and the objective lens 10 are disposed. Reflecting surfaces of the galvano mirror and the polygon mirror of the scanning unit 64 are disposed at positions substantially conjugate with the pupil.

The beam splitter 62 is disposed between the emitting unit 61 and the focusing lens 63. At a reflection side of the beam splitter 62, a condenser lens 66, a confocal opening 67 disposed at a position conjugate with the fundus, and a SLO photodetector 68 are disposed to constitute a confocal optical system.

The laser light (the measurement light or the fixation light) from the emitting unit 61 is transmitted through the beam splitter 62, and then reaches the scanning unit 64 via the focusing lens 63, where a reflecting direction of the laser light is changed by driving of the galvano mirror and the polygon mirror. The laser light reflected by the scanning unit 64 is transmitted through the dichroic mirror 40 via the relay lens 65, and is then collected on the fundus via the objective lens 10.

The laser light reflected from the fundus (the measurement light) passes through the objective lens 10, the relay lens 65, the galvano mirror and the polygon mirror of the scanning unit 64, and the focusing lens 63, and is reflected by the beam splitter 62. Then, the laser light is collected by the condenser lens 66, and then is detected by the photodetector 68 via the confocal opening 67. A photo-receiving signal outputted from the photodetector 68 is inputted into the control unit 70, and the control unit 70 obtains the front image of the fundus based on the photo-receiving signal. The obtained front image is stored in the memory 72. The obtainment of the SLO fundus image is performed by scanning the laser light in the vertical direction (an auxiliary scanning direction) on the fundus with the use of the galvano mirror of the scanning unit 64, and scanning the laser light in the horizontal direction (a main scanning direction) on the fundus with the use of the polygon mirror of the scanning unit 64.

The control unit 70 is connected with a display monitor 75 in order to control an image displayed thereon. In addition, the control unit 70 is connected with the memory (a storing unit) 72, an operation unit 74 for making various operations, the scanning driving mechanism 51, the scanning driving mechanism 52, the reference-mirror driving unit 50, a first driving mechanism 63a arranged to move the focusing lens 63 in the optical axis direction, a second driving mechanism 24a arranged to move the focusing lens 24 in the optical axis direction, and other members.

The control unit 70 forms the tomographic image of the fundus by performing image processing based on a photo-receiving signal outputted from the photodetector 83 and the front image of the fundus by performing image processing based on the photo-receiving signal outputted from the photodetector 68.

The operation unit 74 operated by an examiner is provided with a mouse 74a defining an operation member for various operations, photographing switches 74b, a key board, and other members. The mouse 74a coordinates with the display on the monitor 75, and is used for setting a current scanning position with the measurement light, setting a current presenting position of the fixation target, and other operations. For the control unit 70, the memory 72, the operation unit 74, and the monitor 75, dedicated members defined by devices may be used, or a personal computer (PC) may be used.

A description of obtainment of the front image and the tomographic image of the fundus in the apparatus having the configuration described above will be provided below. First, the examiner instructs the examinee to gaze at the fixation lamp, and performs alignment of the apparatus using a joystick (not shown) such that the measurement optical axis L1 is positioned at a pupil center of the eye E while observing an anterior-segment observation image of the eye E on the monitor 75 that is picked up by an anterior-segment observation camera (not shown). When the alignment with respect to the eye E is complete, the front image by the SLO optical system 300 (the SLO fundus image) becomes obtainable and the SLO fundus image shows up on the monitor 75. The examiner performs focusing while observing the SLO fundus image on the display monitor 75, and then clicks an automatic optical-path-length adjusting button on the monitor 75 using the mouse 74a.

Upon output of a trigger signal for starting automatic optical-path-length adjustment (automatic OPL adjustment), the control unit 70 controls driving of the reference-mirror driving unit 50 to move the reference mirror 31 and adjusts the optical path length of the reference light so as to obtain the fundus tomographic image.

To be more specific, the control unit 70 moves the reference mirror 31 from a predetermined initial position and searches for a position at which the fundus tomographic image is obtained. The control unit 70 obtains a tomographic image at the predetermined initial position, and then searches for a position at which the fundus tomographic image is obtained while moving the reference mirror 31 by given steps and sequentially obtaining tomographic images at moved positions.

The control unit 70 judges the presence or absence of the fundus tomographic image based on luminance distribution in the depth direction of the tomographic images that are sequentially obtained. For example, the presence or absence of the fundus tomographic image is judged based on whether a maximum luminance value of the luminance distribution is greater than a given threshold value. If it is judged that the fundus tomographic image is present, the control unit 70 specifies a position where the maximum luminance value is detected as an image detecting position P1 of the fundus tomographic image. Then, the control unit 70 calculates a deviation amount L in the depth direction between an optical-path-length adjustment position K that is predetermined in the depth direction (see broken lines K in FIGS. 3A and 3B) and the image detecting position P1, moves the reference mirror 31 so that the deviation amount L becomes 0, and then stops the movement of the reference mirror 31. Thus, a given portion of the fundus tomographic image (e.g., a fundus surface) is displayed at a given display position on the monitor 75 regardless of a distance from the pupil to the fundus of the examinee's eye (see FIG. 2B).

Upon completion of the automatic OPL adjustment described above, the control unit 70 stores in the memory 72 the position of the reference mirror 31 at the completion of the automatic OPL adjustment as positional information on the reference mirror 31 at the time of the obtainment of the fundus tomographic image. In addition, after the automatic OPL adjustment, the control unit 70 adjusts the position of the reference mirror 31 based on an operation signal outputted from the mouse 74a. Accordingly, the examiner can observe the fundus tomographic image at a desired position.

Upon output of a given trigger signal, the control unit 70 stores in the memory 72 image data of the tomographic image and/or the front image in association with identification information on the examinee (e.g., an ID number). The control unit 70 stores in the memory 72 the positional information on the reference mirror 31 at the completion of the automatic OPL adjustment and scanning area information on the measurement light by the scanning unit 23 or the scanning unit 64 (photographing view angle information on the fundus image) as photographing conditions for measuring an actual distance in association with the image data described above. The positional information on the reference mirror 31 may be detected by a position sensor that may be disposed in the vicinity of the reference mirror 31 or may be detected based on a driving amount of the reference-mirror driving unit 50 from a given position.

Figures 2A, 2B:
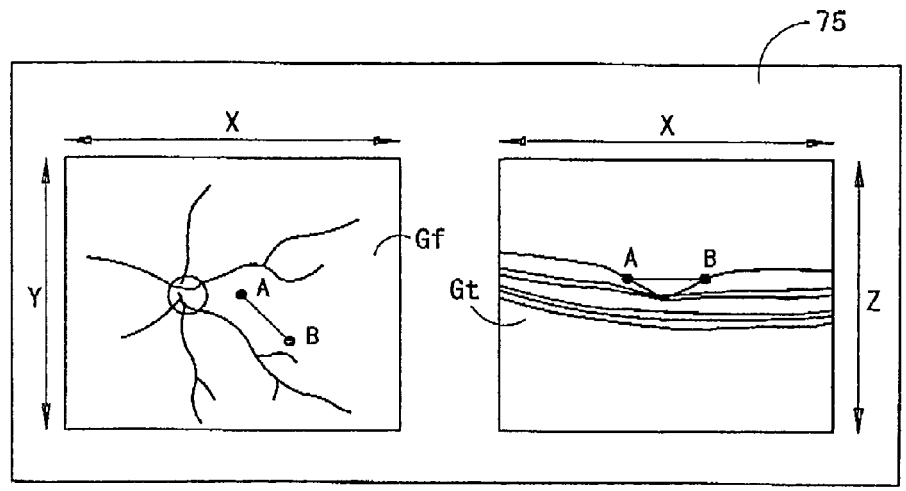
FIGS. 2A and 2B are views for explaining a display screen in an actual distance measurement mode.
Figures 3A, 3B:
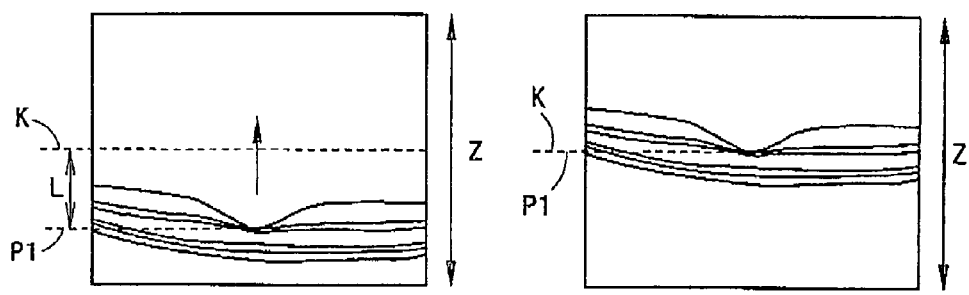
FIGS. 3A and 3B are views for explaining automatic OPL adjustment.

Next, a mode of measuring the actual distance (an actual distance measurement mode) by using the fundus image (the tomographic image or the front image) obtained as described above and the positional information on the reference mirror 31 in relation to the position at which the fundus tomographic image is obtained will be provided. FIGS. 2A and 2B are views for explaining a display screen in the actual distance measurement mode. FIG. 2A shows the measurement using the front image and FIG. 2B shows the measurement using the tomographic image.

If the apparatus is put into the actual distance measurement mode by a given operation, the control unit 70 controls the monitor 75 to display the fundus image (the tomographic image or the front image) stored in the memory 72 (see FIGS. 2A and 2B). Then, the control unit 70 performs arithmetic processing for measuring the actual distance between two points by using a tomographic image Gt or a front image Gf that is displayed on the monitor 75.

To be more specific, two arbitrary points on the fundus image on the monitor 75 (see points A and B in FIGS. 2A and 2B) are designated by an operation of the mouse 74a or other mechanisms (e.g., a click operation), the control unit 70 converts a distance between the designated two points into an actual distance. Alternatively, the control unit 70 may convert a distance between two markers (indicators) that are movably displayed on the fundus image on the monitor 75 into the actual distance. A technique of designating two arbitrary points for the actual distance measurement may be varied and is not limited to the technique described above. For example, a distance from the center or a diameter of a circular marker may be obtained. Alternatively, a shape or area may be calculated based on three or more points including the distance between the two points and the depth direction. In addition, measurement with respect to the X- and Y-directions on a three-dimensional image may be performed (e.g., measurement on a layer thickness map). In addition, a measured portion may be specified by detecting a given portion of the tomographic image by image processing.

Figure 4:
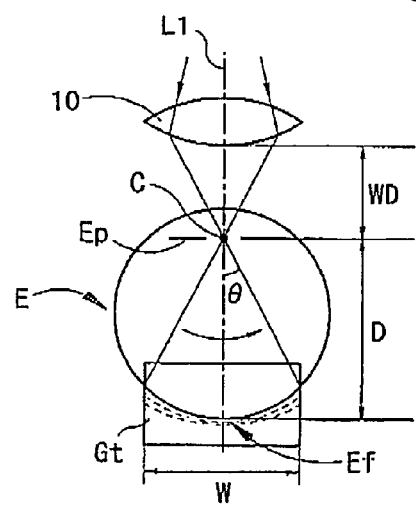
FIG. 4 is a view for explaining measurement of an actual distance.

FIG. 4 is a view for explaining the measurement of the actual distance. A photographing range W of the fundus image (the tomographic image or the front image) is determined based on a half view angle θ (a photographing view angle is 2θ) and a distance D from a pupil Ep to a fundus Ef in an axial direction (W=2×D×tan θ). The photographing view angle 2θ is determined based on a scanning range (a scanning angle) of the measurement light on the fundus defining the center of the pupil Ep as a scanning center C. Accordingly, the control unit 70 calculates the photographing view angle 2θ by using data of the scanning range information on the measurement light in the memory 72. As for the photographing range W of the front image, the vertical limits are determined based on a scanning range of the measurement light in the vertical direction, and the horizontal limits are determined based on the scanning range of the measurement light in the horizontal direction.

The distance D from the pupil Ep to the fundus Ef is calculated as described below. Assuming that an optical path length of the measurement light is represented by LS (for the sake of simplicity, a total optical path length from the light source 27 through the eye E's side surface of the objective lens 10 to the photodetector 83, excluding an optical path length from the objective lens 10 to the fundus Ef), a working distance (from the eye E's side surface of the objective lens 10 to the pupil Ep) is represented by WD, the distance from the pupil Ep to a surface position of the fundus Ef is represented by D, the optical path length of the reference light when the reference mirror 31 is positioned at the predetermined reference position (from the light source 27 through the reference mirror 31 to the photodetector 83) is represented by LR, and a change amount of the optical path length of the reference light when the reference mirror 31 is moved from the given reference position is ΔLR, the following relation is established:

$$LS+2WD+2D=LR+\Delta LR$$

Thus, the distance D is calculated by Equation 1:

$$D=\{LR+\Delta LR-(LS+2WD)\}/2$$

Accordingly, assuming that LS, LR, and WD are fixed values, the distance D is calculated by detecting the change amount ΔLR. The distance D calculated as described above is stored in the memory 72. In this manner, the distance D from the pupil Ep to the fundus Ef that is used for the measurement of the actual distance is calculated based on the positional information on the reference mirror 31 at the time of the tomographic image photographing.

In order to determine the optical path length LR of the reference light, a tomographic image of a calibration optical member having a known distance D (e.g., a model eye) is obtained. The position of the reference mirror 31 when the maximum luminance value in the depth direction is detected at the predetermined optical-path-length adjustment position K is obtained, and the obtained position is determined as the predetermined reference position of the reference mirror 31. Thus, the optical path length LR of the reference light is determined. The change amount ΔLR is calculated by detecting the deviation amount (the movement amount) of the reference mirror 31 from the predetermined reference position. The working distance WD is predetermined based on a focal length on the examinee's eye side of the objective lens 10.

The control unit 70 determines the photographing range W of the fundus image based on the photographing view angle 2θ and the distance D that are obtained as described above. In addition, the control unit 70 calculates the actual distance between the designated two points based on the photographing range W of the fundus image and a coordinate distance between the designated two points on the screen. In the case of the tomographic image, for example, the control unit 70 converts the photographing range in the transverse direction of the tomographic image into the actual distance, and specifies coordinate positions that correspond to the designated two points on the photographed image on the actual distance basis. In the case of the front image, the control unit 70 converts the photographing range in the vertical and horizontal directions of the front image into the actual distance, and specifies coordinate positions that correspond to the designated two points on the photographed image on the actual distance basis. Then, the control unit 70 calculates the distance between the coordinate positions of the designated two points and obtains the actual distance.

In this manner, the actual distance can be measured by using the positional information on the reference mirror 31 in a state that the fundus tomographic image is obtained. Accordingly, the measurement of the actual distance can be performed smoothly by using the tomographic image or the front image obtained by a fundus photographing apparatus.

Although the positional information on the reference mirror 31 at the completion of the automatic OPL adjustment is used for the calculation of the distance D in the above descriptions, it is essential only that the positional information on the reference mirror 31 be obtained in a state that a given portion of the fundus tomographic image is obtained at a given position in the depth direction. For example, if the tomographic image has the deviation amount L with respect to the predetermined optical-path-length adjustment position K (see FIG. 3A), the change amount ΔLR corresponding to the position of the reference mirror 31 is offset by the amount of an optical path length corresponding to the deviation amount L, and the offset change amount ΔLR is used for the calculation of the distance D.

Although an optical path difference between the optical path length of the measurement light and the optical path length of the reference light is adjusted by changing the optical path length of the reference light by the movement of the reference mirror 31 defining a optical-path-length varying optical member in the above descriptions, it is essential only that the optical path difference between the optical path length of the measurement light and the optical path length of the reference light be changed by disposing the optical-path-length varying optical member in any one of the reference light optical path and the measurement light optical path.

The optical path difference between the optical path length of the measurement light and the optical path length of the reference light may be adjusted by changing the optical path length of the measurement light. For example, in the optical system in FIG. 1, the reference mirror 31 is fixed, and the optical path length of the measurement light is changed with respect to the optical path length of the reference light by integrally moving the relay lens 24 and the fiber end portion 39b. In this case, the reference light optical path may be configured by using only the optical fiber.

In the case of changing the optical path length of the measurement light, the distance D is calculated by using a change amount ΔLS of the optical path length of the measurement light at the time when the optical-path-length varying optical member disposed in the measurement optical path is moved from the predetermined reference position.

Although the photographing range is determined by arithmetic processing in the above descriptions, it is also preferable that a table showing a relation between the positional information on the optical-path-length varying optical member at the time of the obtainment of the fundus tomographic image and the photographing range is prestored in the memory 72, and the photographing range that corresponds to the positional information is retrieved from the table.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An ophthalmic photographing apparatus comprising:
    an interference optical system arranged to divide light emitted from a first light source into measurement light and reference light, direct the measurement light to a fundus of an examinee's eye, direct the reference light to a reference optical system, and photo-receive by a first photodetector interference light that is obtained by combining the measurement light reflected from the fundus and the reference light;
    a first optical scanner disposed in an optical path of the measurement light and arranged to scan the measurement light in two dimensional directions on the fundus;
    a driving unit arranged to move an optical-path-length varying optical member in an optical axis direction, the optical member being disposed in one of the optical path of the measurement light and an optical path of the reference light and being capable of changing an optical path length of one of the measurement light and reference light;
    a photographing control unit arranged to:
    control an operation of the first optical scanner, scan the measurement light on the fundus of the examinee's eye, and obtain a tomographic image based on a photo-receiving signal outputted from the first photodetector, and
    control an operation of the driving unit to adjust a position of the optical-path-length varying optical member based on the obtained tomographic image so as to obtain a fundus tomographic image, and obtain the fundus tomographic image of the examinee's eye; and
    a calculation unit arranged to determine a photographing range of the tomographic image based on positional information of the optical-path-length varying optical member in a state that the fundus tomographic image is obtained, and information on the photographing view angle of the fundus tomographic image.

2. The ophthalmic photographing apparatus according to claim 1, further comprising:
    an observation optical system arranged to direct observation light emitted from a second light source to the fundus of the examinee's eye, and photo-receive by a second photodetector the observation light reflected from the fundus of the examinee's eye; and
    a second optical scanner disposed in an optical path of the observation light and arranged to scan the observation light in the two dimensional directions on the fundus of the examinee's eye,
    wherein the photographing control unit is arranged to control an operation of the second optical scanner to scan the observation light at a given photographing view angle on the fundus of the examinee's eye, and obtain a fundus front image of the fundus of the examinee's eye based on a photo-receiving signal outputted from the second photodetector, wherein
the calculation unit is arranged to determine a photographing range of the fundus front image into an actual distance based on the positional information on the optical-path-length varying optical member in a state that the fundus tomographic image is obtained, and information on the photographing view angle of the fundus front image.

3. The ophthalmic photographic apparatus according to claim 1, wherein the calculation unit is arranged to convert the determined photographing range into an actual distance, and measure a given portion that is specified in the fundus tomographic image.

4. The ophthalmic photographing apparatus according to claim 3, wherein the calculation unit calculates an actual area of the given portion that is specified in the fundus tomographic image.

5. The ophthalmic photographing apparatus according to claim 3, further comprising:
    a monitor arranged to display the fundus tomographic image; and
    an operation input unit arranged to designate at least two points in the fundus tomographic image displayed on the monitor in order to specify the given portion in the fundus tomographic image.

6. The ophthalmic photographic apparatus according to claim 2, wherein the calculation unit is arranged to convert the determined photographing range into an actual distance, and measure a given portion that is specified in the fundus tomographic image.

* * * * *